US009906739B2

(12) United States Patent
Sugano et al.

(10) Patent No.: US 9,906,739 B2
(45) Date of Patent: Feb. 27, 2018

(54) IMAGE PICKUP DEVICE AND IMAGE PICKUP METHOD

(71) Applicant: Mitsubishi Electric Engineering Company, Limited, Tokyo (JP)

(72) Inventors: Tetsuo Sugano, Tokyo (JP); Satoshi Shikita, Tokyo (JP)

(73) Assignee: Mitsubishi Electric Engineering Company, Limited (JP)

(*) Notice: Subject to any disclaimer, the term of this patent is extended or adjusted under 35 U.S.C. 154(b) by 130 days.

(21) Appl. No.: 14/445,766

(22) Filed: Jul. 29, 2014

(65) Prior Publication Data
US 2015/0042774 A1 Feb. 12, 2015

(30) Foreign Application Priority Data
Aug. 6, 2013 (JP) .................................. 2013-163472

(51) Int. Cl.
| H04N 9/67 | (2006.01) |
| H04N 5/225 | (2006.01) |
| H04N 5/33 | (2006.01) |
| A61B 1/00 | (2006.01) |
| A61B 1/04 | (2006.01) |
(Continued)

(52) U.S. Cl.
CPC .......... *H04N 5/332* (2013.01); *A61B 1/0005* (2013.01); *A61B 1/00009* (2013.01); *A61B 1/043* (2013.01); *A61B 1/0638* (2013.01); *G06T 5/50* (2013.01); *G06T 7/0012* (2013.01); *H04N 1/3871* (2013.01); *H04N 5/2256* (2013.01); *H04N 5/2258* (2013.01); *H04N 5/23229* (2013.01); *G06T 2207/10024* (2013.01); *G06T 2207/10048* (2013.01); *G06T 2207/10068* (2013.01)

(58) Field of Classification Search
CPC .. H04N 5/332; H04N 5/2258; H04N 5/23229; A61B 1/00009; A61B 1/043; A61B 1/0638; G06T 2207/10048; G06T 5/50
See application file for complete search history.

(56) References Cited

U.S. PATENT DOCUMENTS

2002/0168096 A1* 11/2002 Hakamata ................. G06T 7/11
382/131

FOREIGN PATENT DOCUMENTS

| JP | 2001178674 | 3/2001 |
| JP | 2001299676 A | 10/2001 |

(Continued)

*Primary Examiner* — Andy Rao
*Assistant Examiner* — Tyler Edwards
(74) *Attorney, Agent, or Firm* — Price Heneveld LLP

(57) ABSTRACT

Provided is an image pickup device capable of facilitating distinction between a normal area and a specific area for a camera for medical or industrial use. The image pickup device for picking up images in a plurality of wavelength bands includes a first image pickup part for picking up an optical image in a near-infrared band, a second image pickup part for picking up an optical image in a visible-light band, an image processing part for performing processing for extracting necessary information from a near-infrared image acquired by the first image pickup part, and a synthesized-image generating part for adding a visible image acquired by the second image pickup part and an image obtained by the image processing part at a predetermined ratio to generate a synthetized image.

19 Claims, 11 Drawing Sheets

(51) Int. Cl.
  *A61B 1/06*   (2006.01)
  *G06T 5/50*   (2006.01)
  *G06T 7/00*   (2017.01)
  *H04N 1/387*  (2006.01)
  *H04N 5/232*  (2006.01)

(56) References Cited

FOREIGN PATENT DOCUMENTS

| JP | 2003164414 A | 6/2003 |
| JP | 2007-75198 | 3/2007 |
| JP | 2011087906 A | 5/2011 |
| JP | 2011131002 | 7/2011 |
| WO | 2011111619 A1 | 9/2011 |

* cited by examiner

183 EXAMPLE OF ARRANGEMENT OF DISPLAY PIXELS OF NEAR-INFRARED FLUORESCENT IMAGE
Y(BRIGHTNESS):C(COLOR)= 1:1

185 BRIGHTNESS PORTION IN NEAR-INFRARED AUTOFLUORESCENT PORTION

184 NEAR-INFRARED AUTOFLUORESCENT PORTION (Y:C=1:1)

IMAGE PICKUP DEVICE AND IMAGE PICKUP METHOD

BACKGROUND OF THE INVENTION

1. Field of the Invention

The present invention relates to an image pickup device and method for acquiring a synthesized image based on a normal image acquired by irradiating a test object with visible light and a special image acquired by irradiating the test object with special light in a camera for medical use or industrial use, for example.

2. Description of the Related Art

In the related art, for example, an endoscope system for observing a tissue in a body cavity is widely known. An electronic endoscope system for picking up an image of a portion to be observed in the body cavity through irradiation of white light to obtain a normal image and displaying the obtained normal image on a monitor screen has been widely put into practical use.

As the endoscope system described above, the following fluorescent endoscope system has been widely put into practical use. Specifically, the fluorescent endoscope system picks up an autofluorescent image emitted from the portion to be observed through irradiation of excitation light along with the normal image, appropriately synthesizes the normal image and the autofluorescent image, and displays the obtained synthesized image on the monitor screen.

In particular, fluorescence observation in a vascular flow or diseased tissue through the intravenous administration of indocyanine green (ICG) is conventionally performed. It is generally known that fluorescence in the range of 830 nm to 840 nm is obtained with respect to irradiation of excitation light in the range of 750 nm to 790 nm. However, the fluorescence has a wavelength band in a near-infrared range. Therefore, an image obtained in the above-mentioned case is a monochrome image. In addition, in this state, visible portions are not simultaneously visible. Thus, some experiences and intuition are required for the observation and diagnosis on the characteristic blood-flow fluorescent image and diseased tissue in a sentinel lymph node.

In view of the situations described above, the following is proposed in a fluorescent endoscope system described in Japanese Patent Application Laid-open No. 2007-75198. Specifically, the normal image (illumination-light image) and the white-light image (fluorescent image) are synthesized to display the obtained synthesized image on the monitor screen.

As in the case of the fluorescent endoscope system described in Japanese Patent Application Laid-open No. 2007-75198, however, the illumination-light image which is a visible-light image and the fluorescent image are simply synthesized at a predetermined brightness ratio. Therefore, characteristic information to be obtained from the fluorescent image is not appropriately obtained. In addition, the synthesized image contains a large amount of unnecessary information. For example, a blood-flow portion emits autofluorescent light by an excitation-light source through the administration of indocyanine green (ICG). At this time, as a result of reflection of the autofluorescence wavelength light by a peripheral area of the blood-flow portion, even a portion other than the blood-flow portion frequently looks as if the portion emits fluorescent light. Therefore, the obtained synthesized image has low visibility because not only a desired specific portion is not clearly displayed but also even an unnecessary portion is displayed.

SUMMARY OF THE INVENTION

The present invention has been made in view of the problems described above, and has an object to provide an image pickup device and an image pickup method, which enable acquisition of a synthesized image showing a state of a target of image pickup in a more visible manner.

According to one embodiment of the present invention, there is provided an image pickup device for picking up images in a plurality of wavelength bands, including: a plurality of image pickup parts for picking up optical images in the plurality of wavelength bands; image processing part for performing processing for extracting necessary information from an image in a first wavelength band among the images in the plurality of wavelength bands acquired by the plurality of image pickup parts; and synthesized-image generating part for adding an image in a second wavelength band except for the image in the first wavelength band acquired by the plurality of image pickup parts and the image in the first wavelength band obtained by the image processing part at a predetermined ratio to generate a synthesized image.

According to one embodiment of the present invention, the synthesized image showing the state of the target of image pickup in a more visible manner can be acquired.

DETAILED DESCRIPTION OF THE PREFERRED EMBODIMENTS

Now, an image pickup device and an image pickup method according to the present invention are described by means of each of embodiments where the image pickup device is applied to a rigid scope system, referring to the accompanying drawings. In each of the embodiments, the same or corresponding portions are denoted by the same reference symbols, and the overlapping description thereof is herein omitted.

First Embodiment

Figure 1:
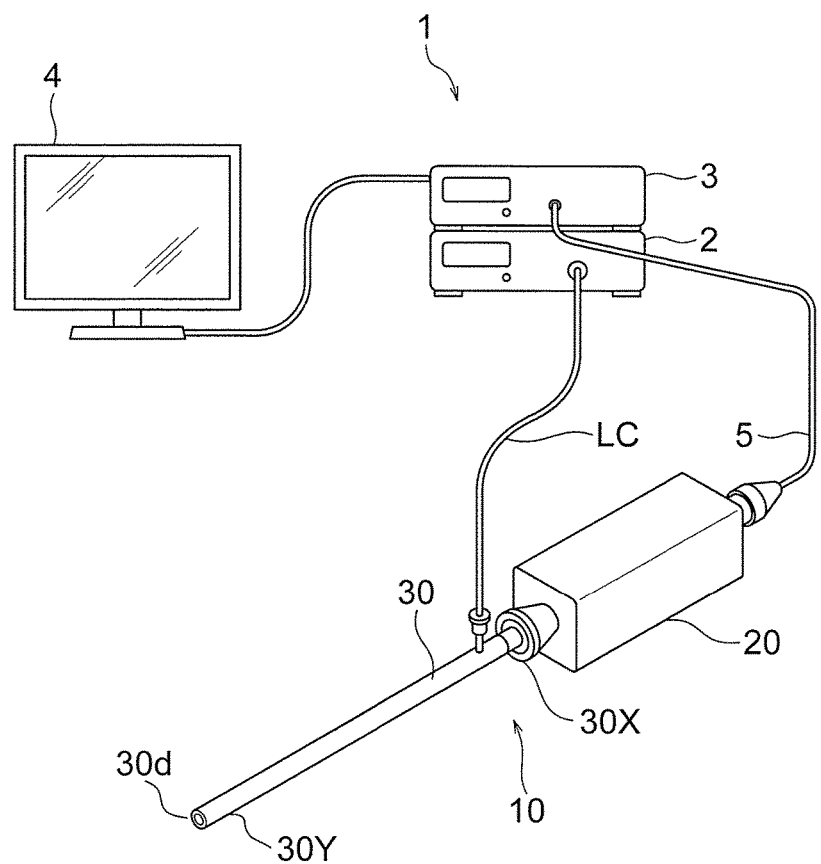
FIG. 1 is a configuration diagram of a rigid scope system to which an image pickup device according to an embodiment of the present invention is applied.
Figure 2:
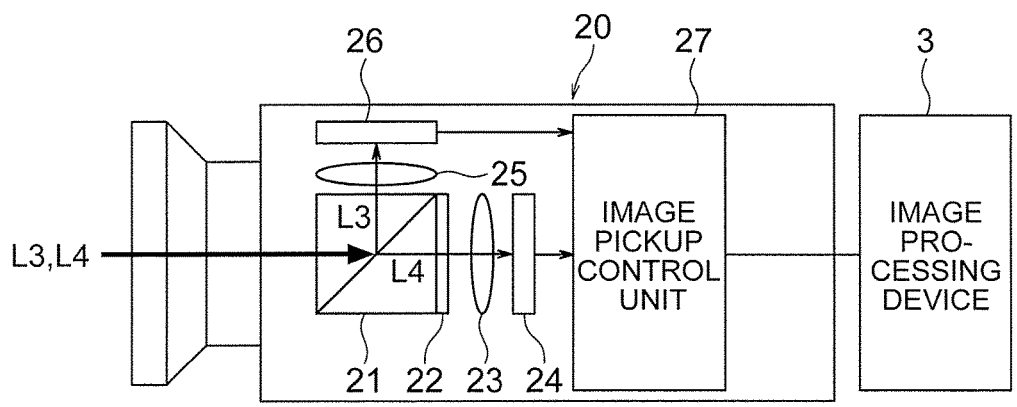
FIG. 2 is a diagram illustrating an example of a schematic configuration of an image pickup unit illustrated in FIG. 1.
Figure 3:
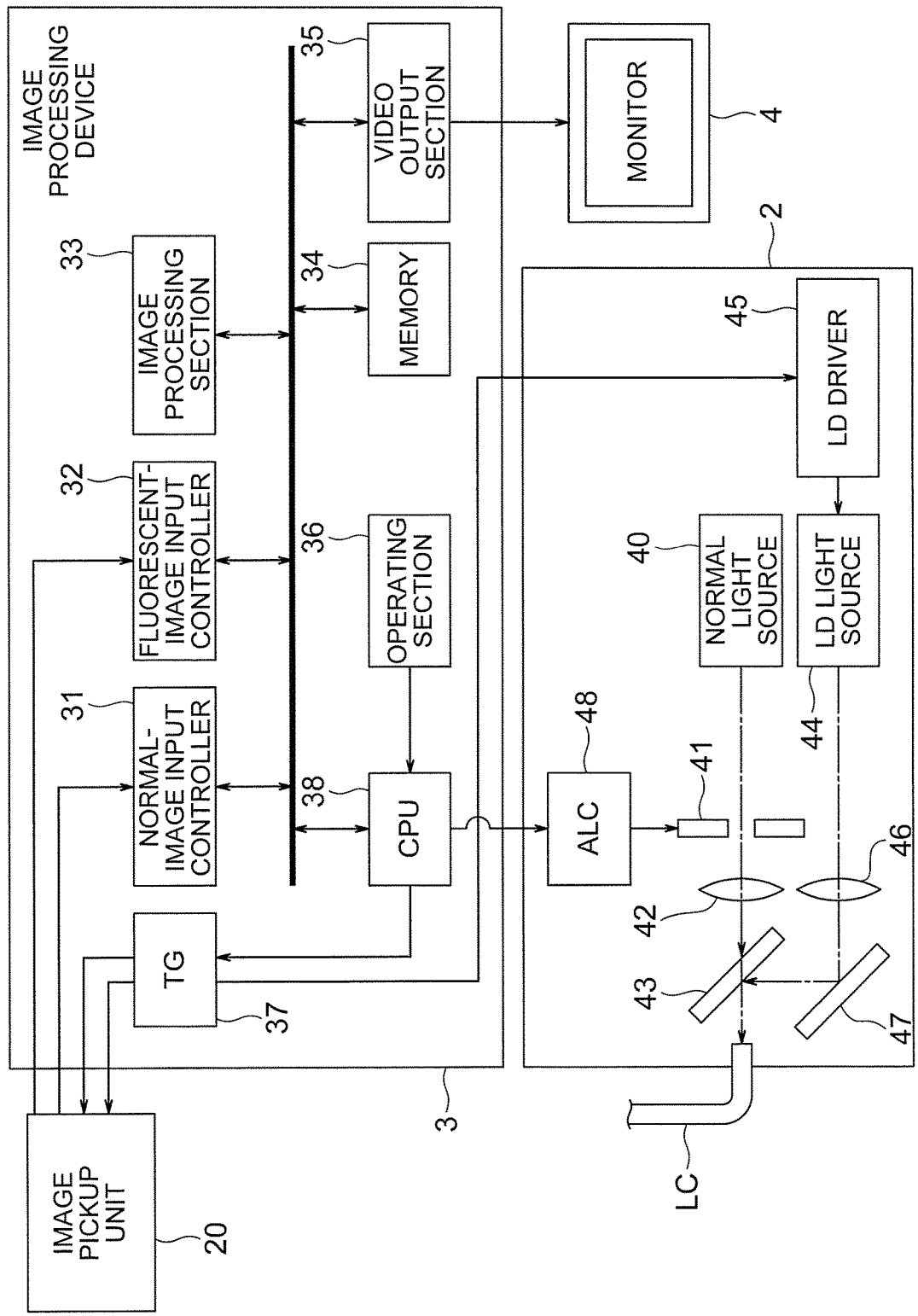
FIG. 3 is a diagram illustrating an example of a schematic configuration of an image processing device and a light source device illustrated in FIG. 1.
Figure 4:
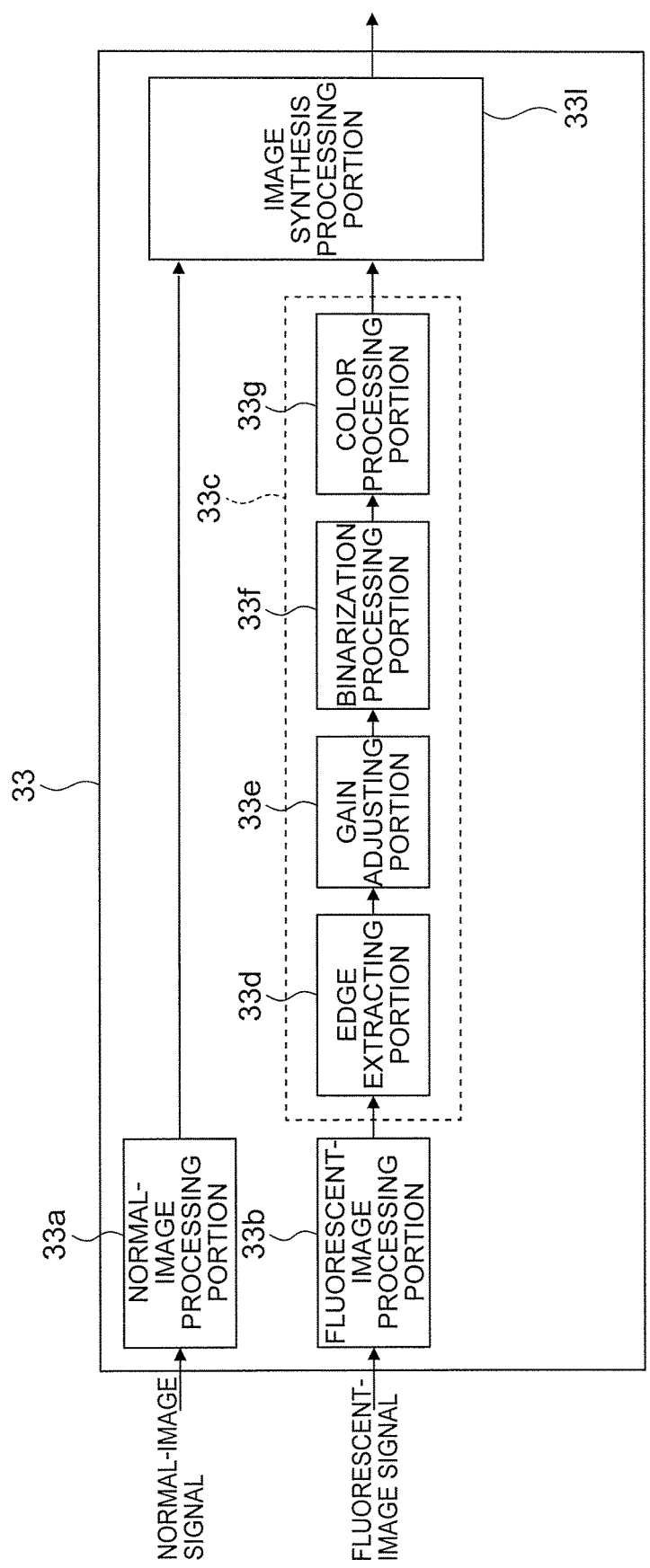
FIG. 4 is a diagram illustrating an example of a more specific configuration of an image processing section illustrated in FIG. 3 according to a first embodiment of the present invention.
Figure 5:
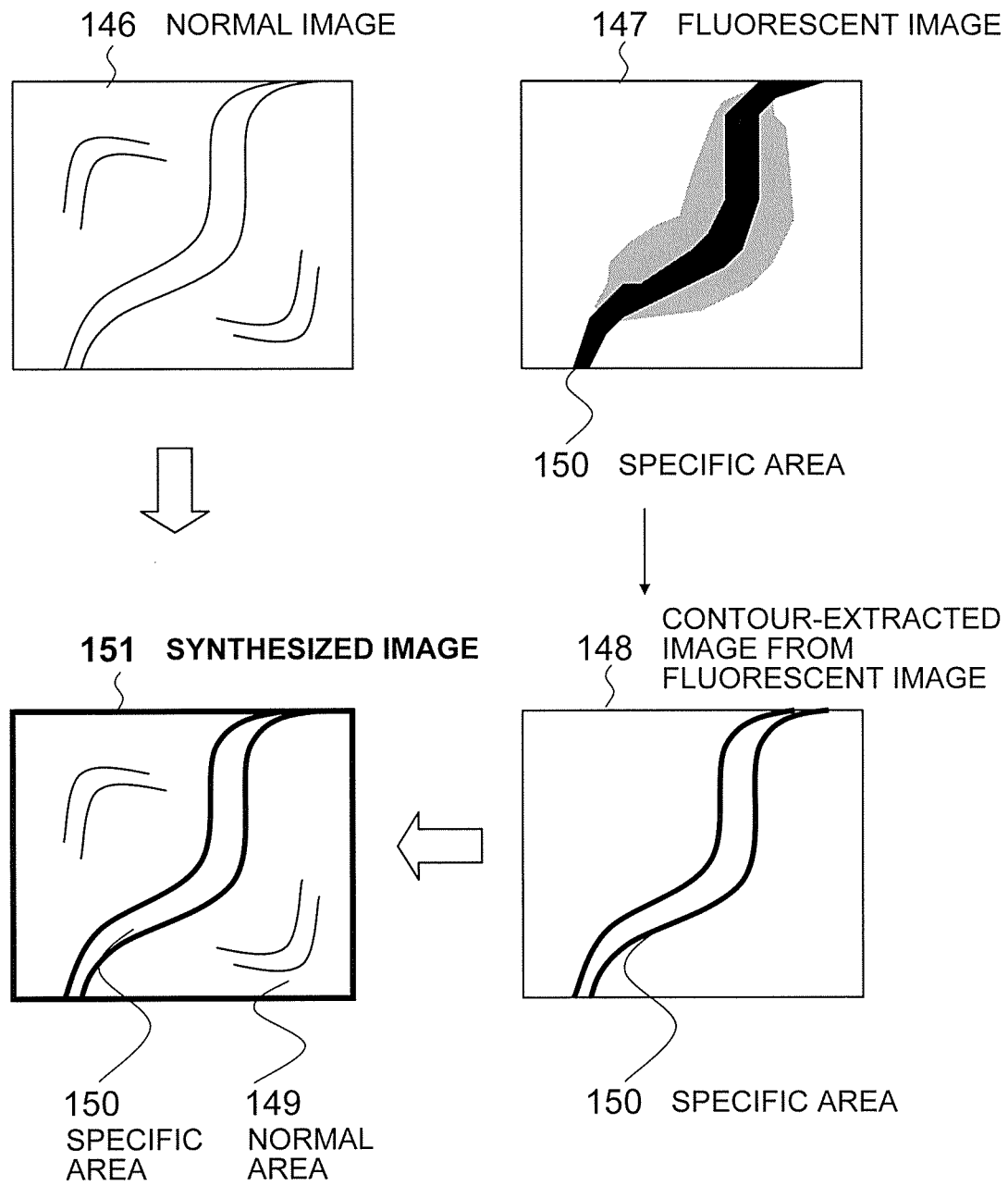
FIG. 5 is a diagram illustrating an example of a process of synthesizing a normal image and a contour-extracted image extracted from a fluorescent image according to the first embodiment of the present invention.

FIG. 1 is a configuration diagram of a rigid scope system to which an image pickup device according to an embodiment of the present invention is applied, FIGS. 2 to 4 are configuration diagrams of parts illustrated in FIG. 1, and FIG. 5 illustrates an example of image synthesis according to the present invention.

A rigid scope system 1 illustrated in FIG. 1 includes a light source device 2, a rigid scope image pickup device 10, an image processing device 3, and a monitor 4. The light source device 2 simultaneously generates white normal light and special light. The rigid scope image pickup device 10 guides the normal light and the special light generated by the light source device 2 to irradiate a portion to be observed (not shown) with the normal light and the special light, and picks up a normal image based on light reflected from the portion to be observed as a result of the irradiation of the normal light and a fluorescent image based on fluorescence emitted from the portion to be observed as a result of the irradiation of the special light. The image processing device 3 performs predetermined processing on an image signal picked up by the rigid scope image pickup device 10. The monitor 4 displays the normal image, the fluorescent image, and a synthesized image of the portion to be observed based on a display control signal generated by the image processing device 3.

The rigid scope image pickup device 10 includes a hard insertion portion 30 and an image pickup unit 20, as illustrated in FIG. 1. The hard insertion portion 30 is to be inserted into an abdominal cavity. The image pickup unit 20 picks up the normal image and the fluorescent image of the portion to be observed which is irradiated with light guided by the hard insertion portion 30.

The hard insertion portion 30 and the image pickup unit 20 are detachably connected to each other in the rigid scope image pickup device 10. In the rigid scope image pickup device 10, the hard insertion portion 30 has a connecting portion provided on a camera side 30X. For example, by fitting the connecting portion into an opening portion formed on the image pickup unit 20, the image pickup unit 20 and the hard insertion portion 30 are connected detachably.

The hard insertion portion 30 is a portion which is inserted into the abdominal cavity when the interior of the abdominal cavity is photographed. The hard insertion portion 30 is formed of a hard material and has, for example, a cylindrical shape having a diameter of about 5 mm. Inside the hard insertion portion 30, a lens group for forming the images of the portion to be observed is accommodated. The normal image and the fluorescent image of the portion to be observed, which are incident from a distal-end side portion 30Y of the hard insertion portion 30, are input to the image pickup unit 20 on the camera side 30X through the lens group.

A cable connecting port is provided on a side surface of the rigid scope image pickup device 10. An optical cable LC is mechanically connected to the cable connecting port. In this manner, the light source device 2 and the hard insertion portion 30 are optically connected to each other through an intermediation of the optical cable LC. The normal light and the special light from the light source device 2 pass through an internal light guide to be radiated from an irradiation window 30d on the portion to be observed.

FIG. 2 is a diagram illustrating an example of a schematic configuration of the image pickup unit 20. The image pickup unit 20 includes a first image pickup system and a second image pickup system. The first image pickup system picks up the fluorescent image of the portion to be observed, which is formed by the lens group provided in the hard insertion portion 30, to generate a fluorescent-image signal of the portion to be observed. The second image pickup system picks up the normal image of the portion to be observed, which is formed by the lens group provided in the hard insertion portion 30, to generate a normal-image signal. The first and second image pickup systems are separated from each other to have two optical axes which cross perpendicularly to each other by a dichroic prism 21 having spectral characteristics for reflecting the normal image and transmitting the fluorescent image.

The first image pickup system includes a special-light cut filter 22, a first imaging optical system 23, and a high-sensitivity image pickup element 24. The special-light cut filter 22 cuts the special light which is reflected by the portion to be observed and then is transmitted through the dichroic prism 21. The first imaging optical system 23 forms a fluorescent image L4 which is radiated from the hard insertion portion 30 to be transmitted through the dichroic prism 21 and the special-light cut filter 22. The high-sensitivity image pickup element 24 picks up the fluorescent image L4 formed by the first imaging optical system 23.

The second image pickup system includes a second imaging optical system 25 and an image pickup element 26. The second imaging optical system 25 forms a normal image L3 which is emitted from the hard insertion portion 30 to be reflected by the dichroic prism 21. The image pickup element 26 picks up the normal image formed by the second imaging optical system 25.

The high-sensitivity image pickup element 24 has a high sensitivity to detect light in a wavelength band of the fluorescent image L4. After converting the light into the fluorescent-image signal, the high-sensitivity image pickup element 24 outputs the obtained fluorescent-image signal. The high-sensitivity image pickup element 24 is a monochrome image pickup element.

The image pickup element 26 detects light in a wavelength band of the normal image L3. After converting the light into the normal-image signal, the image pickup element 26 outputs the normal-image signal. On an image pickup surface of the image pickup element 26, color filters of three primary colors, that is, red (R), green (G), and blue (B), or cyan (C), magenta (M), and yellow (Y) are provided in Bayer arrangement or honeycomb arrangement.

The image pickup unit 20 includes an image pickup control unit 27. The image pickup control unit 27 performs correlated double sampling/automatic gain control (CDS/AGC) processing and A/D conversion processing on the fluorescent-image signal output from the high-sensitivity image pickup element 24 and the normal-image signal output from the image pickup element 26, and then outputs signals obtained by the above-mentioned processing to the image processing device 3 through the cable 5 (see FIG. 1).

FIG. 3 is a diagram illustrating an example of schematic configurations of the image processing device 3 and the light source device 2. The image processing device 3 includes a normal-image input controller 31, a fluorescent-image input controller 32, an image processing section 33, a memory 34, a video output section 35, an operating section 36, a timing generator (TG) 37, and a CPU 38. In practice, the CPU 38 is a microcomputer including a memory (not shown) which stores a program and data therein, and is configured so that an instruction from the operating section 36 can be input thereto.

Each of the normal-image input controller 31 and the fluorescent-image input controller 32 includes a line buffer having a predetermined capacity. The line buffers temporarily store the normal-image signal and the fluorescent-image signal for one frame, which are output from the image pickup control unit 27 of the image pickup unit 20, respectively. Then, the normal-image signal stored in the normal-image input controller 31 and the fluorescent-image signal stored in the fluorescent-image input controller 32 are stored in the memory 34 through a bus.

The normal-image signal and the fluorescent-image signal for one frame, which are read out from the memory 34, are input to the image processing section 33. After performing predetermined image processing on the normal-image signal and the fluorescent-image signal, the image processing section 33 outputs the result obtained by the image processing to the bus. An example of a more specific configuration of the image processing section 33 is illustrated in FIG. 4.

As illustrated in FIG. 4, the image processing section 33 includes a normal-image processing portion 33*a*, a fluorescent-image processing portion 33*b*, an edge extracting unit 33*c*, and an image synthesis processing portion 33*l*. After performing predetermined image processing suitable for the normal image on the input normal-image signal, the normal-image processing portion 33*a* outputs the thus processed normal-image signal. After performing predetermined image processing suitable for the fluorescent image on the input fluorescent-image signal, the fluorescent-image processing portion 33*b* outputs the thus processed fluorescent-image signal. The edge extracting unit 33*c* extracts a contour component from the fluorescent-image signal which has been subjected to the predetermined processing in the fluorescent-image processing portion 33*b*, thereby generating a contour-image signal. The image synthesis processing portion 33*l* synthesizes the normal-image signal output from the normal-image processing portion 33*a* and the contour-image signal output from the edge extracting unit 33*c*.

The edge extracting unit 33*c* includes an edge extracting portion 33*d*, a gain adjusting portion 33*e*, a binarization processing portion 33*f*, and a color processing portion 33*g*. The edge extracting portion 33*d* extracts the contour component from the fluorescent-image signal. The gain adjusting portion 33*e* amplifies the fluorescent-image signal from which the contour component is extracted. The binarization processing portion 33*f* converts the fluorescent-image signal which has been subjected to the gain adjustment into two values indicating black and white. The color processing portion 33*g* converts a brightness signal into a color signal for the fluorescent-image signal which has been subjected to the binarization processing. Detailed processing contents by the respective portions of the image processing section 33 are described later.

The normal-image signal, the fluorescent-image signal, and the synthesized-image signal, which are output from the image processing section 33, are input to the video output section 35 through the bus. The video output section 35 performs predetermined processing on the above-mentioned signals to generate a display control signal, and then outputs the generated display control signal to the monitor 4.

The operating section 36 receives input of various operation instructions and control parameters by an operator. The TG 37 outputs a drive pulse signal for driving the high-sensitivity image pickup element 24 and the image pickup element 26 of the image pickup unit 20, and an LD driver 45 of the light source device 2, which is described later. The CPU 36 controls the entire device.

As illustrated in FIG. 3, the light source device 2 includes a normal light source 40, a condenser lens 42, and a dichroic mirror 43. The normal light source 40 emits normal light (white light) L1 having a wavelength in a broadband in the range of about 400 nm to 700 nm. The condenser lens 42 condenses the normal light L1 emitted from the normal light source 40. The dichroic mirror 43 transmits the normal light L1 condensed by the condenser lens 42 and reflects special light L2 described later so that the normal light L1 and the special light L2 enter an incident end of the optical cable LC. As the normal light source 40, for example, a xenon lamp is used.

When light at 700 nm to 800 nm in the range from a visible band to a near-infrared band is used and indocyanine green (ICG) is used as a fluorescent dye, the light source device 2 includes an LD light source 44, the LD driver 45, a condenser lens 46, and a mirror 47. The LD light source 44 emits near-infrared light at 750 nm to 790 nm as the special light L2. The LD driver 45 drives the LD light source 44. The condenser lens 46 condenses the special light L2 emitted from the LD light source 44. The mirror 47 reflects the special light L2 condensed by the condenser lens 46 toward the dichroic mirror 43.

For the special light L2, a wavelength in a narrower band than the normal light having a wavelength in the broadband is used. The special light L2 is not limited to the light in the above-mentioned wavelength band. The light to be used as the special light L2 is appropriately determined depending on the kind of fluorescent dye or the type of biological tissue to be autofluorescent.

The light source device 2 is optically connected to the rigid scope image pickup device 10 through the optical cable LC.

FIG. 3 illustrates normal-light control sections 41 and 48 to be controlled by the CPU 38.

Next, an operation of the system according to the first embodiment is described. First, after the hard insertion portion 30 connected to the optical cable LC and the cable 5 are mounted to the image pickup unit 20, the light source device 2, the image pickup unit 20, and the image processing device 3 are powered on to be driven.

Next, the hard insertion portion 30 is inserted into the abdominal cavity by the operator, and thus a distal end of the hard insertion portion 30 is located in the vicinity of the portion to be observed.

The normal light L1 emitted from the normal light source 40 of the light source device 2 enters the hard insertion portion 30 through the condenser lens 42, the dichroic mirror 43, and the optical cable LC, and is then radiated on the portion to be observed through the irradiation window 30d of the hard insertion portion 30. On the other hand, the special light L2 emitted from the LD light source 44 of the light source device 2 enters the hard insertion portion 30 through the condenser lens 46, the mirror 47, the dichroic mirror 43, and the optical cable LC, and is then radiated on the portion to be observed through the irradiation window 30d of the hard insertion portion 30 simultaneously with the normal light. For the simultaneous irradiation, irradiation time periods of the normal light and the special light are not required to perfectly coincide with each other. The irradiation time periods need to only at least partially overlap each other.

Then, the normal image based on the light reflected by the portion to be observed through the irradiation of the normal light L1 is picked up, while the fluorescent image based on the fluorescence emitted from the portion to be observed through the irradiation of the special light L2 is picked up simultaneously with the normal image.

More specifically, for picking up the normal image, the normal image L3 based on the light reflected by the portion to be observed through the irradiation of the normal light L1 enters the distal-end side 30Y of the rigid scope image pickup device 10, is guided by the lens group provided inside, and is emitted toward the image pickup unit 20.

The normal image L3 that has entered the image pickup unit 20 is reflected by the dichroic prism 21 in a perpendicular direction toward the image pickup element 26, is formed on the image pickup surface of the image pickup element 26 of the second imaging optical system 25, and is sequentially picked up by the image pickup element 26 at a predetermined interval. In this embodiment, it is assumed that the normal image is picked up at a frame rate of 30 fps.

After being subjected to the correlated double sampling/automatic gain control (CDS/AGC) processing and the A/D conversion processing in the image pickup control unit 27, the normal-image signals sequentially output from the image pickup element 26 are sequentially output to the image processing device 3 through the cable 5.

On the other hand, for picking up the fluorescent image, the fluorescent image L4 based on the fluorescence emitted from the portion to be observed through the irradiation of the special light enter the distal-end side 30Y, is guided by the lens group provided therein, and is emitted toward the image pickup unit 20.

The fluorescent image L4 that has entered the image pickup unit 20 passes through the dichroic prism 21 and the special-light cut filter 22, is then formed by the first imaging optical system 23 on an image pickup surface of the high-sensitivity image pickup element 24, and is picked up by the high-sensitivity image pickup element 24 at a predetermined interval. In this embodiment, the fluorescent image is picked up at a frame rate of, for example, 5 to 30 fps.

After being subjected to the correlated double sampling/automatic gain control (CDS/AGC) processing and the A/D conversion processing in the image pickup control unit 27, the fluorescent-image signals sequentially output from the high-sensitivity image pickup element 24 are sequentially output to the image processing device 3 through the cable 5.

Next, a method of generating the synthesized image based on the normal-image signals and the fluorescent-image signals picked up by the image pickup unit 20 as described above is described referring to FIGS. 3 and 4. First, processing before the image synthesis is described.

First, pre-processing for the normal-image signal is described. After being temporarily stored in the normal-image input controller 31, the normal-image signal input to the image processing device 3 is stored in the memory 34. Then, the normal-image signal for each one frame, which is read out from the memory 34, is output to the image processing section 33.

The normal-image signal input to the image processing section 33 is subjected to gradation correction processing and processing such as noise removal in the normal-image processing portion 33a.

Next, pre-processing for the fluorescent-image signal is described. After being temporarily stored in the fluorescent-image input controller 32, the fluorescent-image signal input to the image processing device 3 is stored in the memory 34. Then, the fluorescent-image signal for each one frame, which is read out from the memory 34, is output to the image processing section 33.

The fluorescent-image signal input to the image processing section 33 is subjected to processing such as noise removal in the fluorescent-image processing portion 33b.

The fluorescent-image signal is first subjected to processing for extracting necessary information before being synthesized with the normal-image signal. A process of the processing is now described.

The contour component such as a blood vessel or diseased tissue is extracted as the necessary information from the fluorescent-image signal in the edge extracting portion 33d.

After the contour component is extracted, the fluorescent-image signal is amplified in the gain adjusting portion 33e. When the detected contour component is faint, the fluorescent-image signal is adjusted by the gain adjusting portion 33e.

After being subjected to the gain adjustment, the fluorescent-image signal is input to the binarization processing portion 33f so as to be subjected to threshold-value processing for the purpose of further extracting the necessary information. The fluorescent-image signals are converted into two values indicating black and white by the threshold-value processing. As a method of determining the threshold value, a mode method or a differential histogram method is used. Alternatively, a threshold value may be directly input from the operating section 36. Moreover, the binarization processing is not necessarily required to be performed. The fluorescent-image signal may be directly output to the color processing portion 33g.

Figure 12:
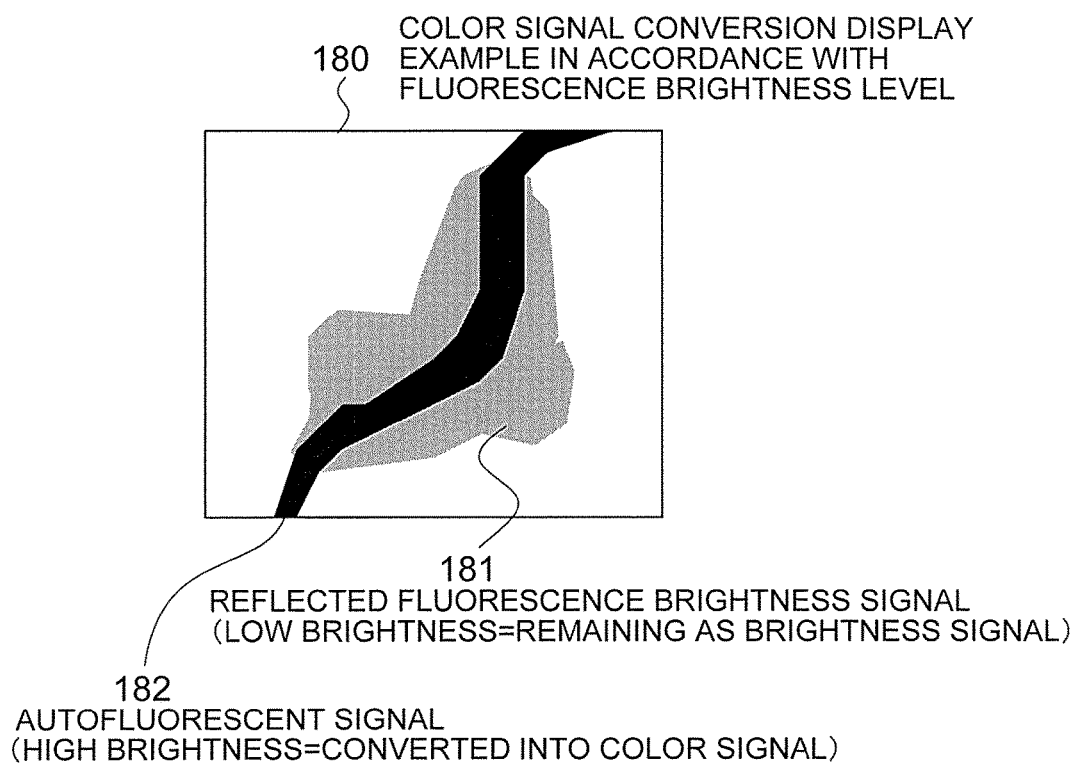
FIG. 12 is a diagram illustrating a color signal conversion display example in accordance with a fluorescent brightness according to the present invention.
Figure 13:
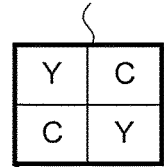
FIG. 13 is a diagram illustrating a color signal conversion display example in accordance with a pixel display position according to the present invention.
Figure 13:
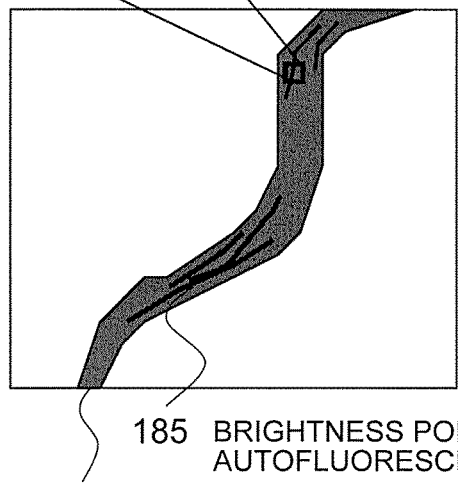

After being subjected to the binarization processing, the fluorescent-image signal is input to the color processing portion 33g where the fluorescent-image signal is subjected to the color processing. The fluorescent-image signal may be subjected to the synthesizing processing with the normal-image signal without the color processing. In such a case, however, there is a possibility that the contour of the fluorescent image may be less visible because the fluorescent-image signal is a monochrome signal. Therefore, the brightness signal is converted into a color signal. For the selection of a color, a color which makes the contour portion after the synthesis more visible may be automatically selected from color components of the normal-image signal which is a target of synthesis (for example, the CPU 38 stores a table of appropriate more visible colors for the color components of the normal-image signal in the memory so that the color processing portion 33g is controlled in accordance with the table to perform the color selection). Alternatively, the color may be directly input through the operating section 36. In this case, in view of the achievement of both visibility of a characteristic portion and a resolution, for example, the brightness signals are not all converted into the color signals. Instead, some brightness signals may be converted, while the other brightness signals are not converted, depending on a brightness level as illustrated in FIG. 12 or an image pickup position as illustrated in FIG. 13. Specifically, in a color-signal conversion display example (180) in accordance with the fluorescence brightness level illustrated in FIG. 12, an autofluorescent portion with a high fluorescence brightness, which is indicated by an autofluorescent signal (182), is converted into the color signal. A portion having a low brightness, which is indicated by a reflected fluorescent brightness signal (181), is left as the brightness signal as the reflected portion. In this manner, the visibility of the autofluorescent portion corresponding to a specific area is increased. Alternatively, as in a display-pixel arrangement example (183) of the near-infrared fluorescent image illustrated in FIG. 13, a fluorescent portion having a high brightness is not entirely converted into the color signals. Instead, conversion and display are performed for each display-pixel unit so as to obtain the brightness signals and the color signals. As a result, a detailed portion of the brightness signals, which has a possibility of being saturated to be invisible if only the image color signals are used as in the case of a near-infrared autofluorescent portion (184) and a brightness portion (185) of the near-infrared autofluorescent portion, can be displayed simultaneously. A distribution and a level of the brightness and the colors illustrated in FIG. 13 only need to be set as appropriate values in accordance with conditions. It is apparent that the brightness portion shown in FIG. 13 may be set to zero so as to overlap the visible image.

Next, image synthesis processing is described. The normal-image signal is input from the normal-image processing portion 33a to the image synthesis processing portion 33l, whereas the contour-image signal is input from the edge extracting unit 33c to the image synthesis processing portion 33l. The image synthesis processing portion 33l synthesizes the contour-image signal and the normal-image signal at a predetermined ratio.

A synthesized-image signal Cs is generated by adding a normal-image signal Cv and a fluorescent-image signal Ci after weighting ($\alpha$ and $\beta$) (in this case, the contour-image signal is treated as the fluorescent-image signal for convenience). For example, the synthesized-image signal is generated in accordance with the following calculation equation.

$$Cs = \alpha \times Cv + \beta \times Ci$$

Then, the synthesized-image signal generated in the image synthesis processing portion 33l is output to the video output section 35. The video output section 35 performs predetermined processing on the input synthesized-image signal to generate the display control signal, and then outputs the display control signal to the monitor 4. Then, the monitor 4 displays a synthesized image as illustrated in FIG. 5 based on the input display control signal.

FIG. 5 illustrates a process of synthesizing a normal image (146) and a contour-extracted image (148) extracted from a fluorescent image (147). The normal image (146) is a visible image. The contour-extracted image (148) contains a contour portion of a specific area (150), which is obtained as the necessary information from the fluorescent image (147). By synthesizing the normal image (146) and the contour-extracted image (148), a synthesized image A (151) containing the specific area (150) and a normal area (149) is obtained.

As illustrated in FIG. 5, when the white light is radiated, the white light is uniformly reflected. Therefore, the normal image (146) is obtained from the second image pickup system. On the other hand, when the excitation light is radiated, the autofluorescence is radiated from the specific area (150) such as a blood vessel or diseased tissue. Therefore, the fluorescent image (147) is obtained from the first image pickup system. Before the generation of the synthesized image, a predetermined brightness change is detected from the fluorescent image (147). Then, the contour-image signal is extracted as the necessary information to obtain the contour-extracted image (148). Thereafter, the contour-extracted image (148) is synthesized with the normal image (146). As a result, an image with a clearly displayed contour portion of the specific area (150) such as a blood vessel or diseased tissue can be obtained.

Moreover, the fluorescent image (147) corresponds to the brightness signals. Therefore, when the extracted signal is synthesized with the normal image (146), it is conceivable that the obtained image has low visibility in some cases. Therefore, after, for example, the brightness signals are partially or entirely converted into the color signals, the synthesis is performed. As a result, the specific area such as diseased tissue can be more easily clearly displayed. In this case, when the color signals to be obtained after the conversion can be arbitrarily selected externally, the specific area becomes more clearly displayed. For the synthesis of the extracted signals, flashing is performed for predetermined time, or the brightness level or a hue is variably set to be controlled. In this manner, the visibility of the specific area can be further improved. The above-mentioned processing is performed in the color processing portion 33g, the image synthesis processing portion 33l, an image synthesis processing portion 33q (second embodiment), and an image superimposing processing portion 33p (third embodiment) by control of the CPU 38 and the operating section 36 (color varying part, image flashing part, and image setting part).

In this embodiment, an example of the rigid scope system such as a laparoscope has been described. However, it is apparent that the present invention can also be applied to systems other than the rigid scope. By connecting an external device meeting general standards of, for example, a C mount, to the camera side 30X, which is an external optical system connecting portion for the image pickup unit 20 illustrated in FIG. 1, systems other than the rigid scope can be used. It is apparent that a system which is capable of varying an image pickup range from a wide angle to a narrow angle as the connection of a zoom lens can be constructed as an example of application. Further, as a completely different system, the present invention may be used for connection to microscopes. In the case of medical microscopes among the microscopes, a system including a light source for ICG excitation light already exists. As an example of application of the image pickup device of the present invention, the system including the light source for ICG excitation light is a recommended system example featuring both the functions.

Moreover, as a system configuration, there is an example where the light source for image pickup is formed integrally as illustrated in FIGS. 1 to 3. However, the system configuration is not limited thereto. The light source may be of type which radiates light externally or injects light by a fiber. Moreover, the kind of light source is not limited to a discharge light source such as a xenon lamp, and may also be a semiconductor device such as a high-brightness LED. It is apparent that a laser may be used on the presupposition that safety can be ensured. The light source may be arranged to take advantages of the respective types of light source.

For example, xenon is used for visible light in a broadband, and an inexpensive LED or a laser in view of high efficiency is used for infrared light.

Further, the method of extracting the necessary information from the image signal is not limited to that described above. Any method may be used as long as the same effects are obtained. For example, a necessary portion such as a bloodstream portion may be extracted by combining a function of detecting only a blood vessel through pattern recognition.

Moreover, there are an image synthesizing technique using addition and an image superimposing technique using superimposing to obtain a desired output image. However, the technique is not limited to those described above. Any method may be used. Moreover, an image generation example where the images are synthesized at the predetermined ratio is described as an example. In this case, the predetermined ratio is not particularly important, and is not defined by the contents of the present invention. Therefore, any ratio may be used without problem as long as a desired output image is obtained after the extraction of the necessary information.

The method described in the image processing block diagram referred to above is an example of the present invention. It is apparent that any method may be used as long as the output image is generated after the extraction of the necessary information. When image processing is performed electrically, processing with hardware such as a dedicated device or an individual circuit, processing with software using a central processing unit (CPU), or both thereof may be used.

The optical system configuration is not limited to that illustrated in FIG. 2. For example, a near-infrared light path may be provided on a reflection side of a dichroic mirror, whereas a visible light path may be provided on a transmission side of the dichroic mirror. Any configuration may be used as long as an individual picked-up image is obtained.

Figure 11:
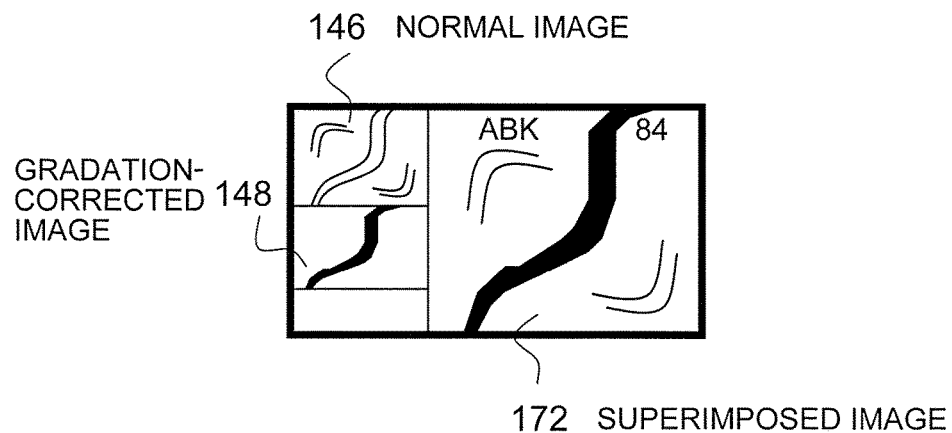
FIG. 11 is a diagram illustrating an example of an output image according to the present invention.
Figure 14:
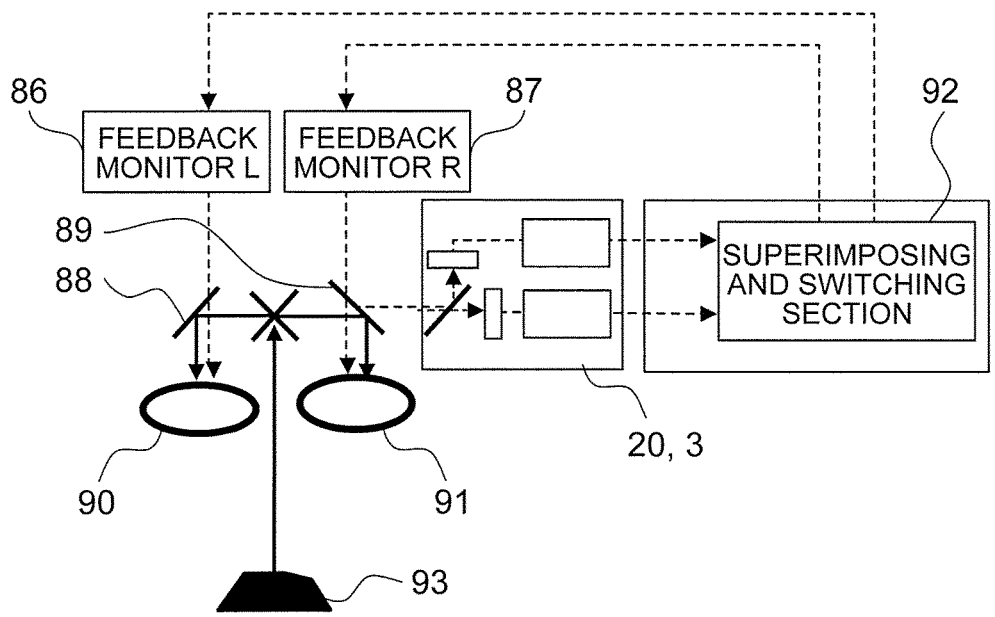
FIG. 14 is a diagram illustrating an example of image superimposing including an optical system according to the present invention.

Further, for example, as illustrated in FIG. 14, the extracted image signal may be converted into an optical image in the visible range by using a display monitor so as to feedback the extracted image signal to the optical system, and then the obtained optical image may be superimposed on an original (actual) visible-light image obtained by an objective lens 93 of the microscope. In FIG. 14, a superimposing mirror L 88 and a superimposing mirror R 89 are used as superimposing part. However, any means may be used as long as the superimposing is performed in the same manner. In this manner, for example, the superimposed image obtained by superimposing the near-infrared light image and the visible-light image can be observed at eyepiece portions of the microscope. In FIG. 14, two monitors, that is, a feedback monitor L 86 and a feedback monitor R 87 are used for dimensional display. However, only one monitor is sufficient. Moreover, not only the near-infrared image but also the superimposed image with the visible-light image may be fed back to the eyepiece portions. At this time, the superimposing at the superimposing mirrors may be performed or may be omitted. Further, the actual optical image and the fed-back image may be simultaneously displayed so as to be shifted in position as illustrated in FIG. 11. As a result, image display with higher visibility and higher functions can be performed for the specific area. In FIG. 11, the normal image (which is the same as the actual optical image) (146), the gradation-corrected image (contour-extracted image) (148), a superimposed image (172) are simultaneously displayed.

The feedback monitor L 86 and the feedback monitor R 87 constitute near-infrared image signal conversion part for changing the obtained near-infrared image signal into the near-infrared visible-light image through photoelectric conversion. Further, the feedback monitors L 86 and R 87, and the superimposing mirrors L 88 and R 89 constitute near-infrared visible-light image superimposing part for changing the obtained near-infrared image signal into the near-infrared visible-light image through photoelectric conversion and superimposing the obtained near-infrared visible-light image on the original visible-light image.

A brief description is given referring to FIG. 14. The original visible-light image (actual optical image) from the objective lens 93 is reflected by the superimposing mirrors L 88 and R 89 respectively to eyepiece portions L 90 and R 91 and also toward the image pickup unit 20 and the image processing device 3. The operator views the original visible-light image from a side below the eyepiece portions L 90 and R 91 in FIG. 14. Each of the normal image, the fluorescent image, and the synthesized image which are processed as described above on the image pickup unit 20 and image processing device 3 side, or the display control signal of each of the images is then input to a superimposing and switching section 92. In the superimposing and switching section 92, the images are superimposed and switched so that the normal image, the fluorescent image, and the synthesized image are respectively displayed on the feedback monitors L 86 and R 87 in a predetermined layout. Thereafter, the display control signal for the display is output. Then, display is performed on the feedback monitors L 86 and R 87 based on the display control signal from the superimposing and switching section 92. As a result, the operator who is located below the eyepiece portions L 90 and R 91 in FIG. 14 to view the image can view the original visible-light image, the image on the feedback monitor L 86, and the image on the feedback monitor R 87 simultaneously.

Further, in the description given above, two kinds of the image pickup parts are used. However, the number, type, and pixel size of image pickup elements are not limited as long as the characteristic information can be extracted from the image which corresponds to the essence of the present invention, to generate the output image. Moreover, in order to obtain the desired output image, the system may extract the necessary information from the input image signal to obtain the output image without being limited to the image pickup part.

Second Embodiment

Figure 6:
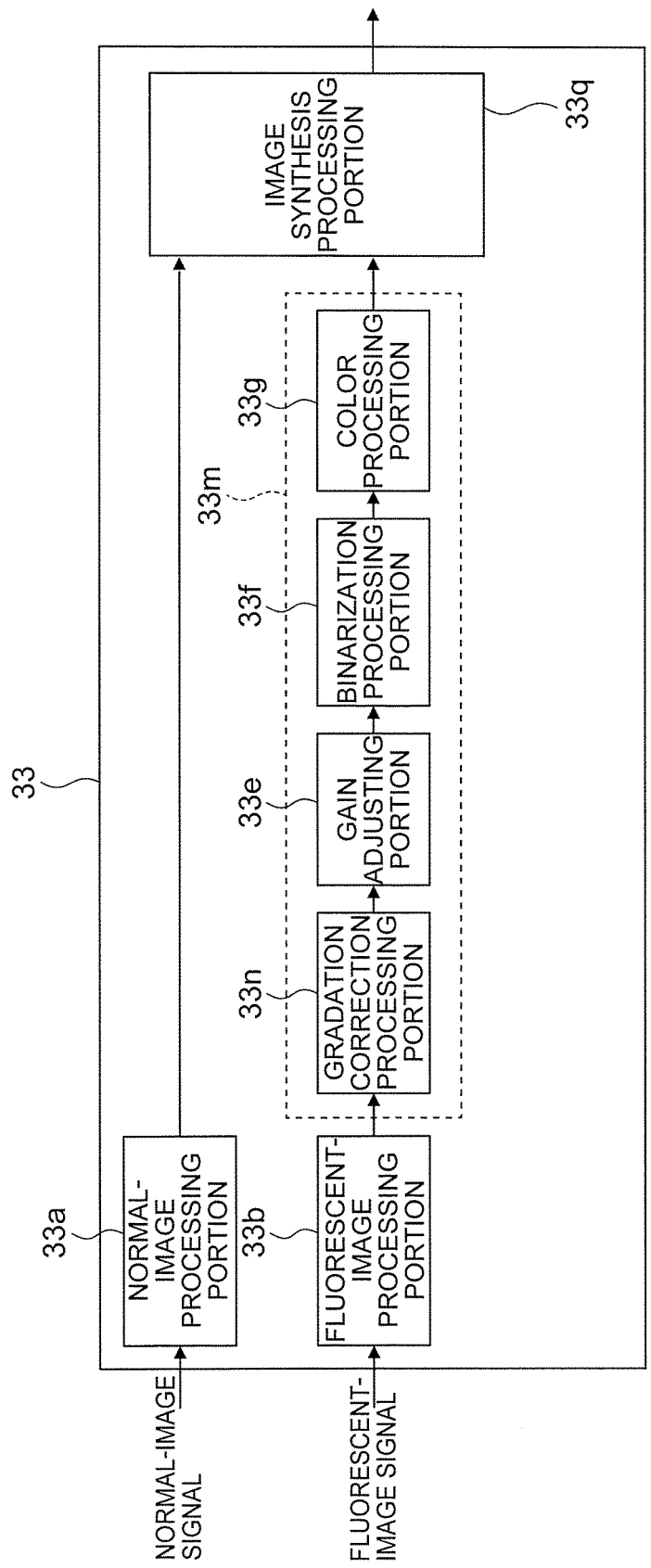
FIG. 6 is a diagram illustrating an example of a more specific configuration of the image processing section illustrated in FIG. 3 according to a second embodiment of the present invention.
Figure 7:
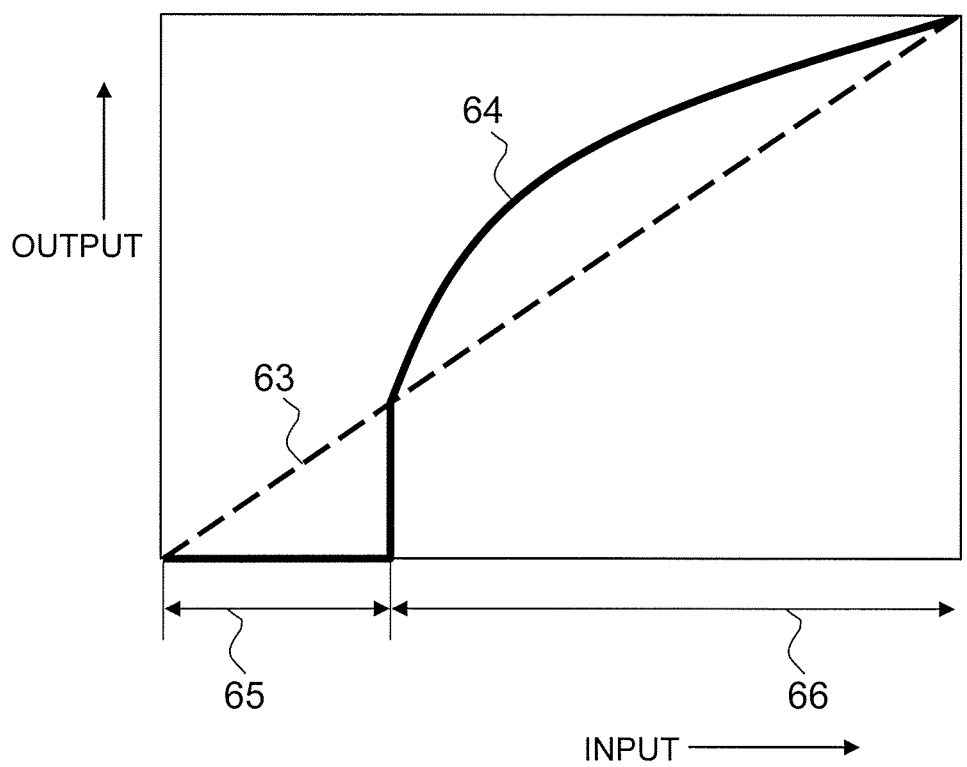
FIG. 7 is a graph showing an example of a characteristic of correction processing according to the second embodiment of the present invention.
Figure 8:
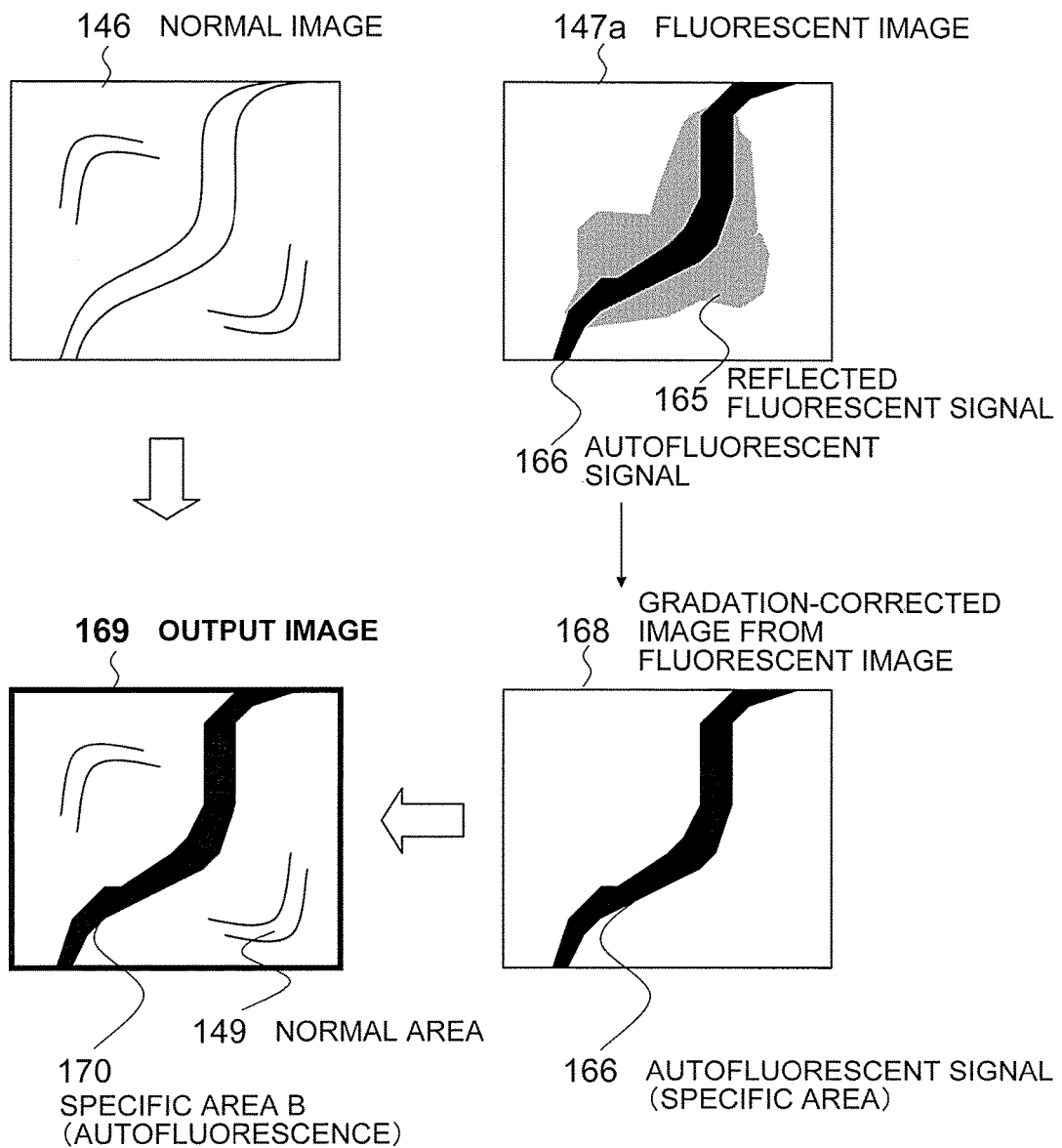
FIG. 8 is a diagram illustrating an example of a process of synthesizing the normal image and a gradation-corrected image extracted from the fluorescent image according to the second embodiment of the present invention.

Now, an image pickup device according to a second embodiment of the present invention is described. A basic configuration of the rigid scope system to which the image pickup device according to the second embodiment is applied is the same as that illustrated in FIG. 1. Moreover, basic configurations of the light source device 2 and the image processing device 3 are the same as those illustrated in FIGS. 2 and 3. FIG. 6 illustrates an example of a specific configuration of the image processing section 33 of the image processing device 3 according to the second embodiment, FIG. 7 illustrates an example of characteristics of the correction processing according to the second embodiment, and FIG. 8 illustrates an example of the image synthesis according to the second embodiment.

In FIG. 6, the image processing section 33 includes the normal-image processing portion 33a, the fluorescent-image processing portion 33b, a gradation correction processing unit 33m, and an image synthesis processing portion 33q.

The normal-image processing portion 33a performs predetermined image processing suitable for the normal image on the input normal-image signal, and outputs the obtained normal-image signal. The fluorescent-image processing portion 33b performs predetermined image processing suitable for the fluorescent image on the input fluorescent-image signal, and outputs the obtained fluorescent-image signal. The gradation correction processing unit 33m performs predetermined processing for extracting necessary information from the fluorescent image on the fluorescent-image signal which is subjected to the predetermined processing in the fluorescent-image processing portion 33b. The image synthesis processing portion 33q synthesizes the normal-image signal output from the normal-image processing portion 33a with a gradation-corrected image signal output from the gradation correction processing unit 33m.

The gradation correction processing unit 33m includes a gradation correction processing portion 33n, the gain adjusting portion 33e, the binarization processing portion 33f, and the color processing portion 33g. The gradation correction processing portion 33n extracts the specific area from the fluorescent-image signal. The gain adjusting portion 33e amplifies the fluorescent-image signal from which the specific area is extracted. The binarization processing portion 33f converts the fluorescent-image signal which has been subjected to the gain adjustment into two values indicating black and white. The color processing portion 33g converts the brightness signal into the color signal for the fluorescent-image signal which has been subjected to the binarization processing.

Next, functions of the system according to the second embodiment are described. An overall operation is the same as that of the embodiment described above, and therefore different parts and characteristic parts are described below.

For the fluorescent-image signal, processing for extracting the necessary information is first performed before the fluorescent-image signal is synthesized with the normal-image signal. A process of the processing is described.

In the gradation correction processing portion 33n, a signal of the specific area such as a blood vessel or diseased tissue is extracted as the necessary information from the fluorescent-image signal. The gradation correction processing portion 33n has an input/output characteristic shown in FIG. 7. The fluorescent image obtained from the first image pickup element (high-sensitivity image pickup element) 24 contains not only the information of the specific area but also not a small amount of information of a periphery thereof and other information. In the fluorescence observation, the autofluorescent signal, which is obtained by the autofluorescence from the blood flow or the diseased tissue bound with protein in plasma through the administration of indocyanine green, is obtained by the first image pickup element 24. The first image pickup element 24 detects even a reflected fluorescent component reflected by the peripheral area in the vicinity as a signal because of the high sensitivity. However, the reflected fluorescent signal in the periphery is faint. Therefore, the reflected fluorescent signal can be eliminated through a certain degree of gradation correction.

FIG. 7 is a characteristic view showing an example of the characteristic of the gradation correction processing portion 33n. The gradation correction characteristic shown in FIG. 7 is expressed as a characteristic of an output with respect to an input. In contrast to a linear characteristic 63 showing the relationship between an input and an output in a one-to-one (proportional) relation by a broken line, for example, a dedicated gradation correction characteristic 64 indicated by a solid line is obtained in the example of the gradation correction processing portion 33n according to the present invention. Specifically, taking advantage of a sufficiently low reflected fluorescent signal level 65 with respect to an autofluorescent signal level 66 contained in the input signal, the gradation correction processing portion 33n is provided with the characteristic so that the reflected fluorescent signal level 65 is not output. In this manner, only the original autofluorescent portion such as the vascular blood flow or the diseased area can be extracted.

After being subjected to the gradation processing, the extracted signal is amplified in the gain adjusting portion 33e. When the detected extracted signal is faint, the extracted signal is adjusted by the gain adjusting portion 33e.

After being subjected to the gain adjustment, the extracted signal is input to the binarization processing portion 33f where the extracted signal is subjected to the threshold-value processing so as to further extract the necessary information. By the threshold-value processing, the fluorescent-image signal is converted into two values indicating black and white. As a method of determining the threshold value, the mode method or the differential histogram method is used. Alternatively, the threshold value may also be directly input through the operating section 36. Moreover, the binarization processing is not necessarily performed. The fluorescent-image signal may be directly output to the color processing portion 33g.

After being subjected to the binarization processing, the fluorescent-image signal is input to the color processing portion 33g where the fluorescent-image signal is subjected to the color processing. The fluorescent-image signal may be directly subjected to the synthesis processing with the normal-image signal without the color processing. However, the fluorescent-image signal is the monochrome signal. Therefore, there is a possibility that the fluorescent image is less visible. Thus, the brightness signal is converted into the color signal. For the selection of the color, the color which makes the fluorescent portion more visible after the synthesis may be automatically selected from the color components of the normal-image signal which is a target. The color may be directly input through the operating section 36. In this case, in view of the achievement of both the visibility of the characteristic portion and the resolution, for example, the brightness signals are not all converted into the color signals. Instead, some brightness signals may be converted, while the other brightness signals are not converted, depending on a brightness level as illustrated in FIG. 12 or an image pickup position as illustrated in FIG. 13. Specifically, in FIG. 12, the autofluorescent portion (182) with the high fluorescence brightness is converted into the color signals. The portion having the low brightness is left as the brightness signal as the reflected portion (181). In this manner, the visibility of the autofluorescent portion corresponding to the specific area is increased. Alternatively, in FIG. 13, the fluorescent portion having a high brightness is not entirely converted into the color signals. Instead, conversion and display are performed for each display-pixel unit (183) so as to obtain the brightness signals and the color signals. As a result, the detailed portion of the brightness signals, which has a possibility of being saturated to be invisible if only the color signals are used, can be displayed simultaneously (184 and 185). The distribution and the level of the brightness and the colors illustrated in FIG. 13 only need to be set as appropriate values in accordance with conditions. It is apparent that the brightness portion shown in FIG. 13 may be set to zero so as to overlap the visible image.

Next, the image synthesis processing is described. The normal-image signal is input from the normal-image processing portion 33a to the image synthesis processing portion 33q, whereas the gradation-corrected image signal is input from the gradation correction processing unit 33m to the image synthesis processing portion 33q. In the image synthesis processing portion 33q, the gradation-corrected image signal and the normal-image signal are synthesized at a predetermined ratio.

The synthesized-image signal Cs is generated by adding the normal-image signal Cv and a fluorescent-image signal Ci1 after weighting ($\alpha$1 and $\beta$1) (in this case, the gradation-corrected image signal is treated as the fluorescent-image signal for convenience).

For example, the synthesized-image signal is generated in accordance with the following calculation equation.

$$Cs=\alpha 1 \times Cv + \beta 1 \times Ci1$$

Then, the synthesized-image signal generated in the image synthesis processing portion 33q is output to the video output section 35. The video output section 35 performs the predetermined processing on the input synthesized-image signal to generate the display control signal, and then outputs the display control signal to the monitor 4. Then, the monitor 4 displays the synthesized image as illustrated in FIG. 8 based on the input display control signal.

FIG. 8 illustrates a process of synthesizing the normal image (146) and a gradation-corrected image (168) extracted from a fluorescent image (147a). The normal image (146) is a visible image. The gradation-corrected image (168) contains an autofluorescent signal (166) (specific area B 170), which is obtained as the necessary information from the fluorescent image (147a). By synthesizing the normal image (146) and the gradation-corrected image (168), an output image (169) containing the specific area B (170) and the normal area (149) is obtained.

As illustrated in FIG. 8, when the white light is radiated, the white light is uniformly reflected. Therefore, the normal image (146) is obtained from the second image pickup system. On the other hand, when the excitation light is radiated, the autofluorescence is radiated from the specific area such as a blood vessel or diseased tissue. Therefore, the fluorescent image (147a) is obtained from the first image pickup system. Before the generation of the synthesized image, the gradation correction processing is performed on the fluorescent image (147a) in accordance with the gradation characteristic shown in FIG. 7 to obtain the gradation-corrected image (168) as the necessary information. Thereafter, the gradation-corrected image (168) is synthesized with the normal image (146). As a result, an image with a clearly displayed specific area B (170) such as a blood vessel or diseased tissue can be obtained.

Moreover, the fluorescent image (147a) corresponds to the brightness signals. Therefore, when the extracted signal is synthesized with the normal image (146), it is conceivable that the obtained image has low visibility in some cases. Therefore, after, for example, the brightness signal is converted into the color signal, the synthesis is performed. As a result, the specific area such as diseased tissue can be more easily clearly displayed. In this case, when the color signal to be obtained after the conversion can be arbitrarily selected externally, the specific area becomes more clearly displayed. For the synthesis of the extracted signals, flashing is performed for predetermined time, or the brightness level or a hue is variably set to be controlled. In this manner, the visibility of the specific area can be further improved.

Other variations are the same as the embodiment described above, and therefore the description thereof is herein omitted.

Third Embodiment

Figure 9:
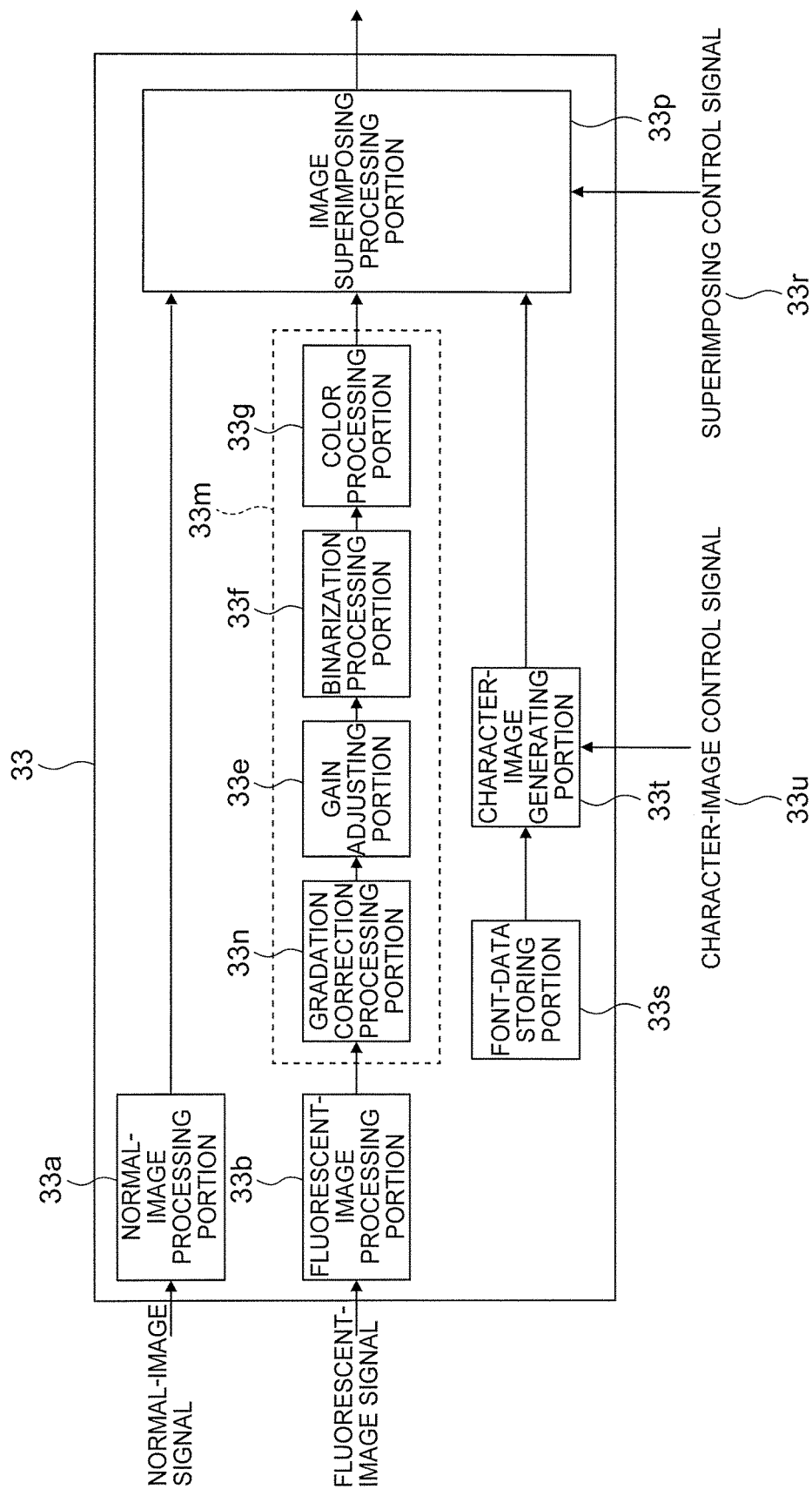
FIG. 9 is a diagram illustrating an example of a more specific configuration of the image processing section illustrated in FIG. 3 according to a third embodiment of the present invention.
Figure 10:
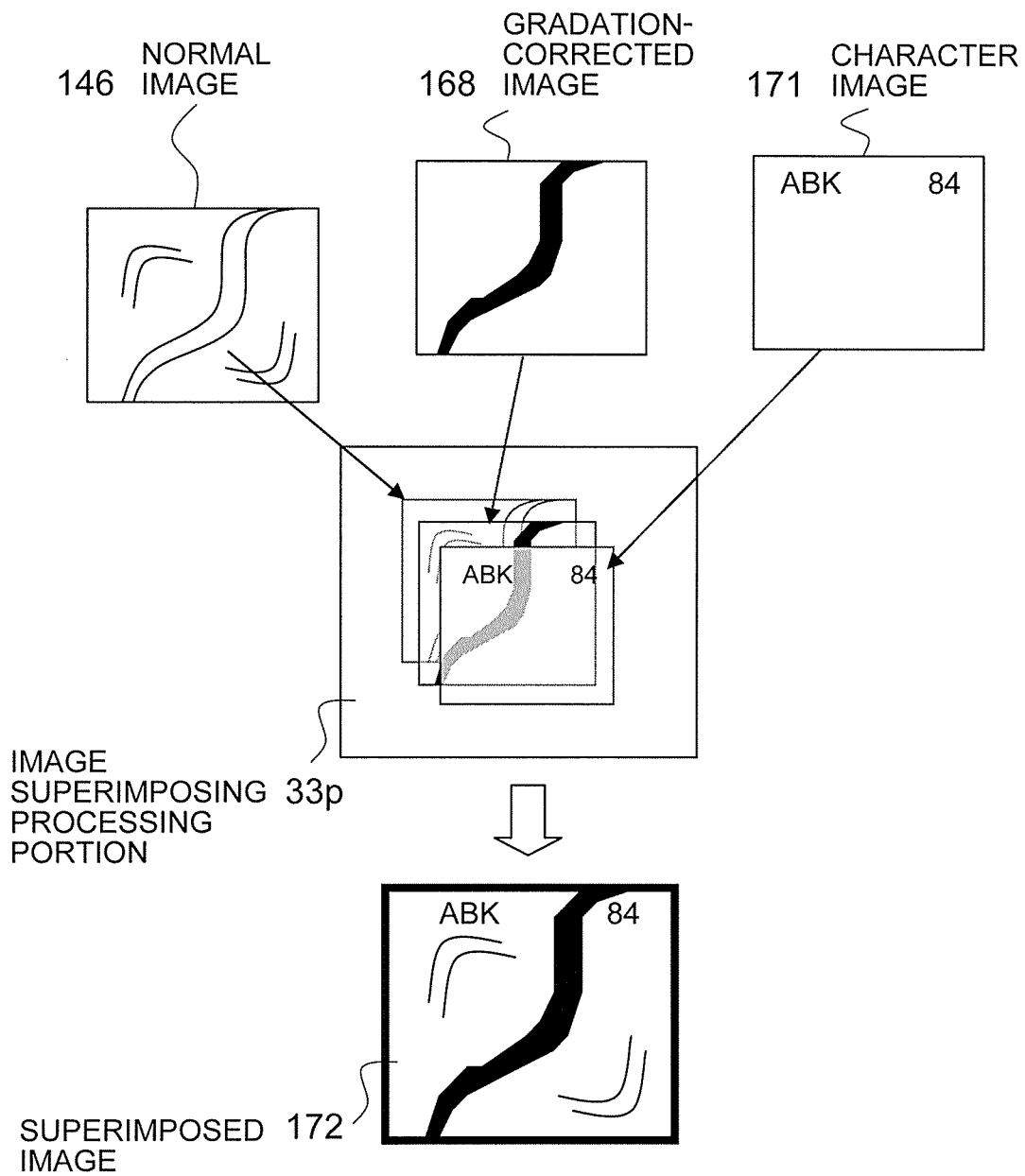
FIG. 10 is a diagram illustrating an example of an operation of an image superimposing processing portion according to the third embodiment of the present invention.

Now, an image pickup device according to a third embodiment of the present invention is described. A basic configuration of the rigid scope system to which the image pickup device according to the third embodiment is applied is the same as that illustrated in FIG. 1. Moreover, basic configurations of the light source device 2 and the image processing device 3 are the same as those illustrated in FIGS. 2 and 3. FIG. 9 illustrates a specific configuration of the image processing section 33 of the image processing device 3 according to the third embodiment, FIG. 7 illustrates characteristics of the correction processing according to the third embodiment, FIG. 8 illustrates an example of the generated image according to the third embodiment, and FIG. 10 illustrates an example of an operation of an image superimposing processing portion.

In FIG. 9, the image processing section 33 includes the normal-image processing portion 33a, the fluorescent-image processing portion 33b, the gradation correction processing unit 33m, and an image superimposing processing portion 33p. The normal-image processing portion 33a performs predetermined image processing suitable for the normal image on the input normal-image signal, and outputs the obtained normal-image signal. The fluorescent-image processing portion 33b performs predetermined image processing suitable for the fluorescent image on the input fluorescent-image signal, and outputs the obtained fluorescent-image signal. The gradation correction processing unit 33m performs predetermined processing for extracting necessary information from the fluorescent image on the fluorescent-image signal which is subjected to the predetermined processing in the fluorescent-image processing portion 33b. The image superimposing processing portion 33p synthesizes the normal-image signal output from the normal-image processing portion 33a with a gradation-corrected image signal output from the gradation correction processing unit 33m.

The gradation correction processing unit 33m includes the gradation correction processing portion 33n, the gain adjusting portion 33e, the binarization processing portion 33f, and the color processing portion 33g. The gradation correction processing portion 33n extracts the specific area from the fluorescent-image signal. The gain adjusting portion 33e amplifies the fluorescent-image signal from which the specific area is extracted. The binarization processing portion 33f converts the fluorescent-image signal which has been subjected to the gain adjustment into two values indicating black and white. The color processing portion 33g converts the brightness signal into the color signal for the fluorescent-image signal which has been subjected to the binarization processing.

The image processing section 33 further includes a character-image generating portion 33t and a font-data storing portion 33s. The character-image generating portion 33t has a connection to a character-image control signal 33u and the font-data storing portion 33s. An output from the character-image generating portion 33t is transmitted to the image superimposing processing portion 33p.

Next, functions of the system according to the third embodiment are described. An overall operation is the same as that of the embodiments described above, and therefore different parts and characteristic parts are described below.

The image superimposing processing which is a feature of this embodiment is described. The processing before the image superimposing processing is basically the same as that of the second embodiment.

The normal-image signal is input from the normal-image processing portion 33a to the image superimposing processing portion 33p, whereas the gradation-corrected image signal is input from the gradation-corrected processing unit 33m to the image superimposing processing portion 33p. The character-image generating portion 33t uses character information in the font-data storing portion 33s from the CPU 38 via the character-image control signal 33u to generate a character image. The character image informs the operator of the necessary information by screen display. The image superimposing processing portion 33p displays the gradation-corrected image signal, the normal-image signal, and the character-image signal as one image by superimposing the above-mentioned signals.

Then, the superimposed (synthetized) image signal generated in the image superimposing processing portion 33p is output to the video output section 35. The video output section 35 performs the predetermined processing on the input synthesized-image signal to generate the display control signal, and outputs the thus generated display control signal to the monitor 4. Then, the monitor 4 displays a superimposed image (172) as illustrated in FIG. 10 based on the input display control signal.

FIG. 10 (see also related FIG. 8) illustrates a process of superimposing the normal image (146) and the gradation-corrected image (168) extracted from the fluorescent image (147a). The normal image (146) is a visible image. The gradation-corrected image (168) contains the autofluorescent signal (166) (specific area B 70), which is obtained as the necessary information from the fluorescent image (147a). By superimposing the normal image (146) and the gradation-corrected image (168), the superimposed image (172) is obtained.

As illustrated in FIG. 8, when the white light is radiated, the white light is uniformly reflected. Therefore, the normal image (146) is obtained from the second image pickup system. On the other hand, when the excitation light is radiated, the autofluorescent is radiated from the specific area such as a blood vessel or diseased tissue. Therefore, the fluorescent image (147a) is obtained from the first image pickup system. Then, before the generation of the synthesized image, the gradation correction processing is performed on the fluorescent image (147a) in accordance with the gradation characteristic shown in FIG. 7 to obtain the gradation-corrected image (168) as the necessary information. Thereafter, the gradation-corrected image (168) is superimposed on the normal image (146). As a result, an image with a clearly displayed specific area B (170) such as a blood vessel or diseased tissue can be obtained.

Moreover, the fluorescent image (147a) corresponds to the brightness signals. Therefore, it is conceivable that the image is sometimes less visible after the extracted signal is superimposed on the normal image (146). Therefore, by superimposing the signals after the brightness signal is converted into the color signal, the specific area such as diseased tissue can be more easily clearly displayed. In this case, when the color signal to be obtained after the conversion can be arbitrarily selected externally, the specific area becomes more clearly displayed. Further, for the synthesis of the extracted signal, flashing is performed for predetermined time, or the brightness level or the hue is variably set to be controlled. In this manner, the visibility of the specific area can be further improved.

As illustrated in FIG. 10, for example, the images are superimposed in the following order in the respective layers. Specifically, the normal image (146) is provided as a lowermost layer, the gradation-corrected image (168) is provided as an intermediate layer, and the character image (171) is provided as an uppermost layer. The image superimposing processing portion 33p does not perform the synthesis processing with simple addition but superimposes the images in a state in which each of the images has an independent layer structure as described above. Therefore, the image to be superimposed on the output image to be displayed can be selected automatically or by a user based on a superimposing control signal 33r which is a control signal. This selection is realized by the CPU 38 or the operating section 36. In this manner, the character image (171) is superimposed as needed, which provides convenience. Moreover, in the above-mentioned structure, the images are present in an independent manner. Therefore, as illustrated in FIG. 11, each of the images can be displayed in an arbitrary size at an arbitrary position in a superimposed manner. As a result, for example, an image desired by the operator who is performing an operation can be more easily obtained.

Other variations are the same as the embodiments described above, and the description thereof is herein omitted.

The present invention is not limited to the embodiments described above, and encompasses all the possible combinations thereof.

The special-light cut filter 22, the first imaging optical system 23, and the high-sensitivity image pickup element 24, which correspond to the first image pickup system, constitute first image pickup part. The second imaging optical system 25 and the image pickup element 26, which correspond to the second image pickup system, constitute second image pickup part. The edge extracting portion 33d and the gradation-correction processing portion 33n constitute image processing part. Each of the image synthesis processing portions 33l and 33q constitutes synthesized-image generating part. The image superimposing processing portion 33p constitutes superimposed-image generating part. The binarization processing portion 33f constitutes threshold-value processing part. The color processing portion 33g constitutes color processing part. The CPU 38, the operating section 36, the color processing portion 33g, the image synthesis processing portion 33l or 33q, and the image superimposing processing portion 33p constitute color varying part, image setting part, and image flashing part. The feedback monitors L 86 and R 87 constitute near-infrared image signal conversion part. The feedback monitors L 86 and R 87 and the superimposing mirrors L 88 and R 89 constitute near-infrared visible-light image superimposing part.

What is claimed is:

1. An image pickup device for picking up images in a plurality of wavelength bands, comprising:
a first image pickup part for picking up an optical image in a near-infrared band, wherein the optical image in the near-infrared band is formed from light fluorescing from tissue;
a second image pickup part for picking up an optical image in a visible-light band, wherein the optical image in the visible-light band is formed from visible light reflecting from the tissue when exposed to white light;
a contour-image extracting part for performing processing for extracting a contour portion from a near-infrared image acquired by the first image pickup part; and a synthesized-image generating part for adding a visible image acquired by the second image pickup part and a contour image obtained through contour extracting processing by the contour-image extracting part at a predetermined ratio to generate a synthesized image.

2. An image pickup device for picking up images in a plurality of wavelength bands, comprising:
a first image pickup part for picking up an optical image in a near-infrared band, wherein the optical image in the near-infrared band is formed from light fluorescing from tissue;
a second image pickup part for picking up an optical image in a visible-light band, wherein the optical image in the visible-light band is formed from visible light reflecting from the tissue when exposed to white light;
a gradation correction processing part for performing gradation correction processing on a near-infrared image acquired by the first image pickup part; and
a synthesized-image generating part for adding a visible image acquired by the second image pickup part and a correction-processed image obtained by the gradation correction processing part at a predetermined ratio to generate a synthesized image.

3. The image pickup device according to claim 1, further comprising:
a threshold-value processing part for binarizing a brightness signal of the near-infrared image to be synthesized.

4. The image pickup device according to claim 1, further comprising:
a color processing part for converting a brightness signal of the near-infrared image to be synthesized into a color signal.

5. The image pickup device according to claim 1, further comprising:
an image setting part for setting a color of the near-infrared image to be synthesized.

6. The image pickup device according to claim 1, further comprising:
an image flashing part for flashing at least one of a brightness signal or a color signal of the near-infrared image to be synthesized.

7. The image pickup device according to claim 1, further comprising:
a color processing part for subjecting the near-infrared image to be synthesized to color processing.

8. An image pickup device for picking up images in a plurality of wavelength bands, comprising:
a first image pickup part for picking up an optical image in a near-infrared band, wherein the optical image in the near-infrared band is formed from light fluorescing from tissue;
a second image pickup part for picking up an optical image in a visible-light band, wherein the optical image in the visible-light band is formed from visible light reflecting from the tissue when exposed to white light;
an image processing part for performing processing for extracting necessary information from a near-infrared image acquired by the first image pickup part;
a superimposed-image generating part for superimposing a visible image acquired by the second image pickup part with an image obtained by the image processing part to generate an output image; and
a threshold-value processing part for binarizing a brightness signal of the near-infrared image to be superimposed.

9. The image pickup device according to claim 8, further comprising:
a color processing part for converting a brightness signal of the near-infrared image to be superimposed into a color signal.

10. The image pickup device according to claim 8, further comprising:
an image setting part for setting a color of the near-infrared image to be superimposed.

11. The image pickup device according to claim 8, further comprising:
an image flashing part for flashing at least one of a brightness signal or a color signal of the near-infrared image to be superimposed.

12. The image pickup device according to claim 8, further comprising:
a color processing part for subjecting the near-infrared image to be superimposed to color processing.

13. The image pickup device according to claim 1, further comprising:
a near-infrared image signal conversion part for converting an obtained near-infrared image signal into a near-infrared visible-light image through photoelectric conversion.

14. The image pickup device according to claim 1, further comprising:
a near-infrared visible-light image superimposing part for converting an obtained near-infrared image signal into a near-infrared visible-light image through photoelectric conversion and superimposing the obtained near-infrared visible-light image on an actual visible-light image.

15. The image pickup device according to claim 1, further comprising:
a color processing part for converting at least some brightness signals of the near-infrared image into the color signal.

16. The image pickup device according to claim 2, further comprising:
a threshold-value processing part for binarizing a brightness signal of the near-infrared image to be synthesized.

17. The image pickup device according to claim 2, further comprising:
a color processing part for converting a brightness signal of the near-infrared image to be synthesized into a color signal.

18. The image pickup device according to claim 2, further comprising:
an image setting part for setting a color of the near-infrared image to be synthesized.

19. The image pickup device according to claim 2, further comprising:
an image flashing part for flashing at least one of a brightness signal or a color signal of the near-infrared image to be synthesized.

* * * * *